United States Patent
Shirai et al.

(10) Patent No.: US 7,721,606 B2
(45) Date of Patent: May 25, 2010

(54) ULTRASONIC TEST METHOD AND ULTRASONIC TEST INSTRUMENT USED FOR THE METHOD

(75) Inventors: Makoto Shirai, Ibaraki (JP); Hiroshi Miyamoto, Chiba (JP); Shigeyuki Matsubara, Osaka (JP)

(73) Assignee: Independent Administrative Institution Japan Aerospace Exploration Agency, Tokyo (JP)

( * ) Notice: Subject to any disclaimer, the term of this patent is extended or adjusted under 35 U.S.C. 154(b) by 324 days.

(21) Appl. No.: 11/667,772

(22) PCT Filed: Nov. 11, 2005

(86) PCT No.: PCT/JP2005/020738

§ 371 (c)(1),
(2), (4) Date: Jan. 18, 2008

(87) PCT Pub. No.: WO2006/051913

PCT Pub. Date: May 18, 2006

(65) Prior Publication Data

US 2008/0127731 A1    Jun. 5, 2008

(30) Foreign Application Priority Data

Nov. 15, 2004    (JP) ............................. 2004-331033

(51) Int. Cl.
*G01N 9/24* (2006.01)
(52) U.S. Cl. .............................. 73/627; 73/597; 73/628
(58) Field of Classification Search .................. 73/627, 73/597, 629, 600, 602
See application file for complete search history.

(56) References Cited

U.S. PATENT DOCUMENTS 4,397,186 A * 8/1983 Phelan et al. ................. 73/584

(Continued)

FOREIGN PATENT DOCUMENTS

JP    01-187447 A    7/1989

(Continued)

OTHER PUBLICATIONS

Notification of Transmittal of Translation of the International Preliminary Report on Patentability; International Application No. PCT/JP2005/020738; Filing Date: Nov. 11, 2005.

(Continued)

*Primary Examiner*—J M Saint Surin
(74) *Attorney, Agent, or Firm*—Rader, Fishman & Grauer PLLC

(57) ABSTRACT

An ultrasonic test method for detecting a defective portion more precisely in a noncontact reflection way, and ultrasonic test instrument used for the method. An ultrasonic wave is transmitted from a transmitter (20 (21)) provided on one side of an object under test, and the reflected wave is received by a receiver (30 (31)) provided on the same side. The ultrasonic wave is transmitted/received through an air layer between the transmitter and the object (100) under test and between the receiver and the object (100). The relative positions of the transmitter (20), the receiver (30), and the object (100) are so determined that the air propagation time ta of the air path (RA) between the transmitter and the receiver is longer than the propagation time tb of the reflected wave in the reflection path (RB). The propagation of the ultrasonic wave through the solid body between the transmitter and the receiver is blocked. This invention is suitable to test laminated material (100) such as a laminate of CFRP (101) and insulation (102) in a noncontact way.

7 Claims, 7 Drawing Sheets

U.S. PATENT DOCUMENTS

| | | | | |
|---|---|---|---|---|
| 4,689,996 | A | * | 9/1987 | Huschelrath .................. 73/643 |
| 5,596,612 | A | * | 1/1997 | Andersson .................. 376/245 |
| 5,619,423 | A | * | 4/1997 | Scrantz ........................ 702/51 |
| 6,761,071 | B2 | * | 7/2004 | Winter ......................... 73/649 |
| 7,614,304 | B2 | * | 11/2009 | Gunasekaran et al. ......... 73/598 |

FOREIGN PATENT DOCUMENTS

| JP | 02-154147 A | 6/1990 |
|---|---|---|
| JP | 3864180 B2 | 10/2006 |

OTHER PUBLICATIONS

Notification Concerning Transmittal of International Preliminary Report on Patentability; International Application No. PCT/JP2005/020738; Filing Dated: Nov. 11, 2005.

Matsubara et al., "Ultrasonic Inspection of CFRP Material Using Air Coupling," Proceeding of Autumn Meeting, pp. 213-214, the Institute of Non-Breaking Testing (2001).

International Search Report.

* cited by examiner

FIG. 3
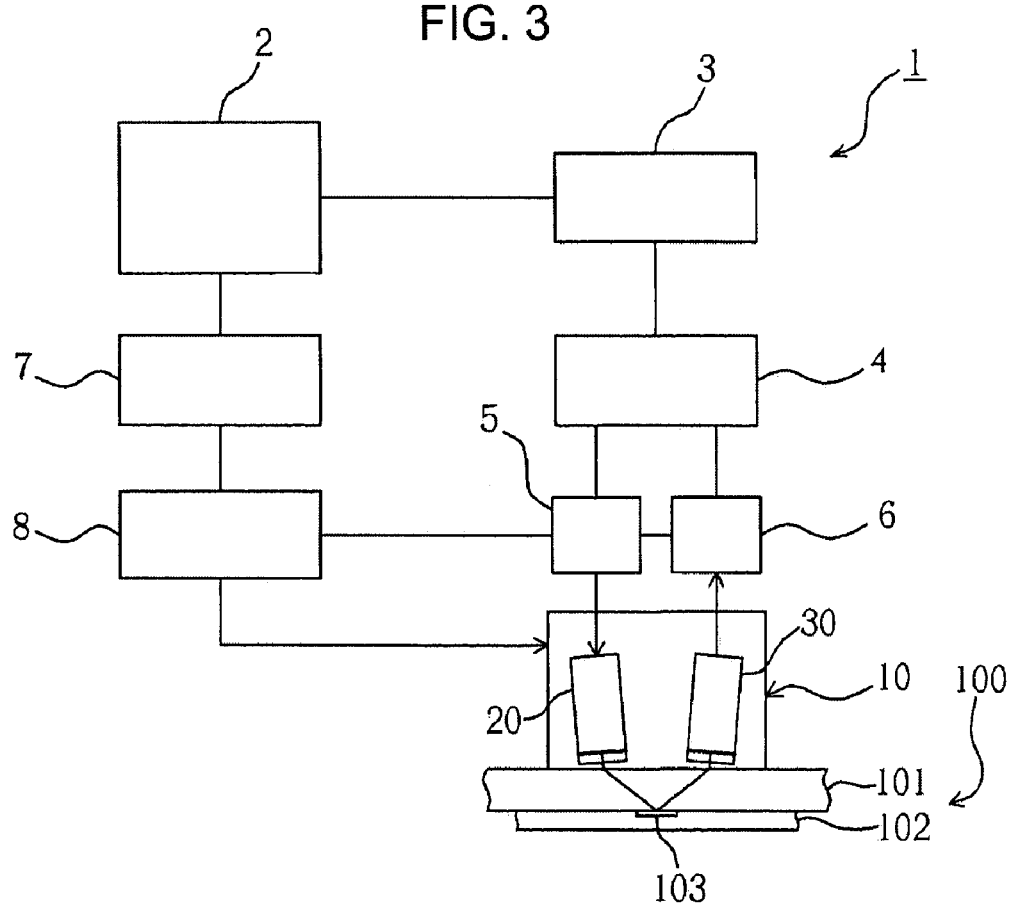
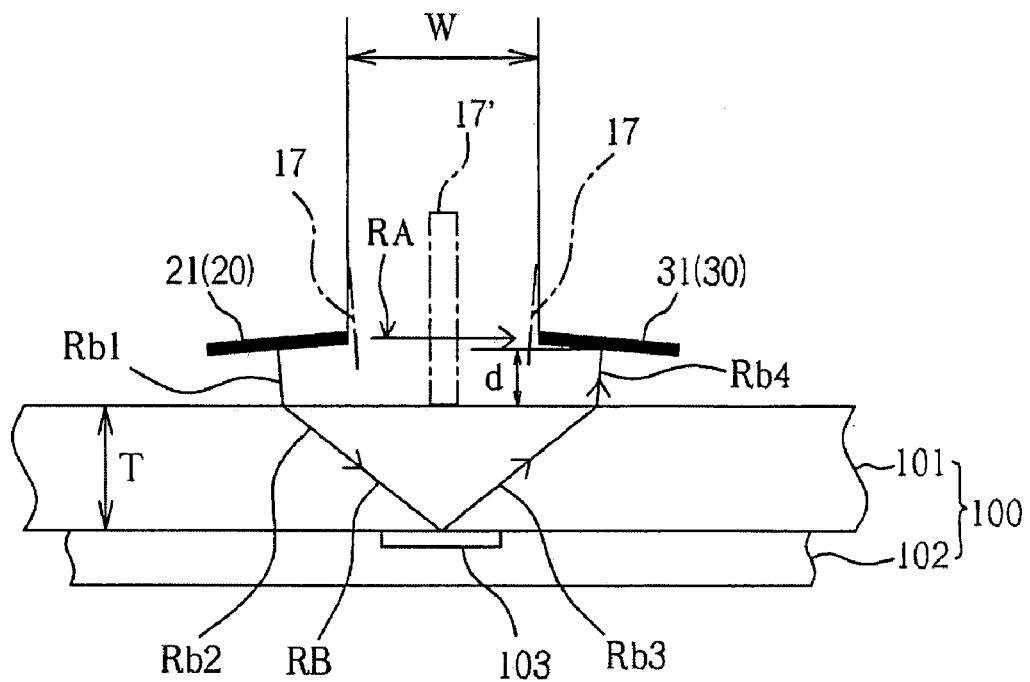
FIG. 4

ULTRASONIC TEST METHOD AND ULTRASONIC TEST INSTRUMENT USED FOR THE METHOD

TECHNICAL FIELD

The present invention relates to an ultrasonic test method and an ultrasonic test instrument for use to conduct the method, which are favorably applicable to an inspection of various materials for disbanding with the use of a reflection technique. More particularly, the present invention relates to an ultrasonic test method and an ultrasonic test instrument for emitting an ultrasonic wave from a probe provided at one side of a test piece to be inspected and receiving its reflection from the test piece with another probe.

BACKGROUND ART

Such an ultrasonic test using the reflection technique is known where the reflection of ultrasonic wave is received from a contact medium examining a target area of the test piece to be inspected. It is common that the reflection of ultrasonic wave is separated with time from the surface reflected waves.

When the ultrasonic test method for inspecting of disbonding is used for examining a layer assembly which has a CFRP (carbon fiber reinforced plastic) material bonded with an insulating layer, it execution is desired in a non-contact mode with no use of a contact medium. In such a mode as shown in FIG. 10, the ultrasonic wave is emitted from a probe 200 and their reflection B from a disbanding defect developed in the interface between the CFRP layer 101 and the insulating layer 102 is received which is however too low in the speed of propagation through the air to separate from but overlap with the surface reflected wave S reflected on the surface of the test piece 100 (the CFRP layer 101) as shown in FIG. 11.

Meanwhile, such a non-contact test method as disclosed in Non Patent Citation 1 using plate waves is proved that when the target area 103 to be inspected in a layer assembly is deep, its defect 103 may hardly be detected.

Non Patent Citation 1: "Ultrasonic inspection of CFRP material using air coupling", by Shigeyuki Matsubara et al, the Institute of non-breakable testing, Japan, Proceeding of Autumn Meeting (Heisei 13), pp. 213-214.

DISCLOSURE OF THE INVENTION (Problem to be Solved by the Invention)

The present invention has been developed in view of the foregoing aspects and its object is to provide an ultrasonic test method and an ultrasonic test apparatus for certainly detecting a defect with the use of a non-contact reflection technique.

(Means for Solving the Problem)

For achievement of the foregoing object, an ultrasonic test method according to the present invention is provided for emitting an ultrasonic wave from a probe provided at one side of a test piece and receiving the reflection of the ultrasonic wave and characterized in that the probe comprises an emitter and a receiver for emitting and receiving the ultrasonic wave through the gaps of air between the emitter and the test piece and between the test piece and the receiver, wherein the emitter, the receiver, and the test piece are relatively located in such a relationship that the duration of time for directly propagating the ultrasonic wave through the gap of air between the emitter and the receiver is longer than the duration of time for propagating the reflection of the ultrasonic wave.

It is common in a plate wave method that the emitter and the receiver are separated from each other because a test piece is oscillated at its entirety. A reflection method permits the emitter and the receiver to be located closer to each other in a normal mode, where the emitter and the receiver may be separated from each other in case that the propagation of ultrasonic waves is disturbed due to disadvantage of a shape. In the plate method, the distance between the emitter and the receiver is a key for the propagation of ultrasonic waves across a test piece. The plate method is different from the method of the present invention in the relationship between the geometrical arrangement and the path of propagation of ultrasonic waves. The present invention has been developed to an achievement only through studying the relationship between the geometrical arrangement and the path of propagation of ultrasonic waves.

FIG. 4 illustrates a direct path RA through the air and a reflection path RB extending from an oscillator 21 to an oscillator 31. The reflection path RB is a sum of two paths Rb1 and Rb4 through the air and two paths Rb2 and Rb3 of the ultrasonic wave incoming and reflecting in the interface between a CFRP material 101 and an insulating layer 102 of a test piece to be inspected. Considering the speed of sound through the test piece, the relationship of $tb<ta$ is established where tb is the duration of time for propagation along the path RB and ta is the duration of time for propagation along the path RA. Accordingly, the reflection of the ultrasonic wave from a defect can be separated from a component of the ultrasonic wave propagated directly through the air.

The method may preferably be modified in which the propagation of the ultrasonic wave through a solid between the emitter and the receiver which are located comparatively close to each other is intentionally interrupted in order to ensure a difference in the time for propagation of the ultrasonic wave through the air. This can be implemented by separately providing a casing for the emitter and a casing for the receiver.

Alternatively, a shielding member may be provided at the interface between the emitter and the receiver in order to increase the distance of the path of propagation through the air, thus allowing the emitter and the receiver to be located closer to each other.

For measuring at any depth in the test piece to be inspected, the emitter and the receiver may be joined movably and separately to a frame.

The present invention is applicable to inspection of a material in layers such as an assembly of a CFRP material and an insulating material bonded together.

An ultrasonic test apparatus for use with the ultrasonic test method depicted above according to the present invention is provided comprising an emitter and a receiver for emitting and receiving the ultrasonic wave through the gaps of air between the emitter and the test piece and between the test piece and the receiver, wherein the emitter, the receiver, and the test piece are relatively located in such a relationship that the duration of time for directly propagating the ultrasonic wave through the gap of air between the emitter and the receiver is longer than the duration of time for propagating the reflection of the ultrasonic wave.

(Advantages of the Invention)

As described, the ultrasonic test method and the ultrasonic test apparatus according to the present invention allow a defect to be certainly detected using a non-contact reflection technique. The other objects, arrangements, and features of the present invention will be apparent from the following description of a preferred embodiment of the present invention.

BRIEF DESCRIPTION OF THE DRAWINGS

FIG. 3 is a block diagram showing the ultrasonic test apparatus according to the present invention;

FIG. 4 is an explanatory view of paths for propagation of ultrasonic waves;

Figure 1:
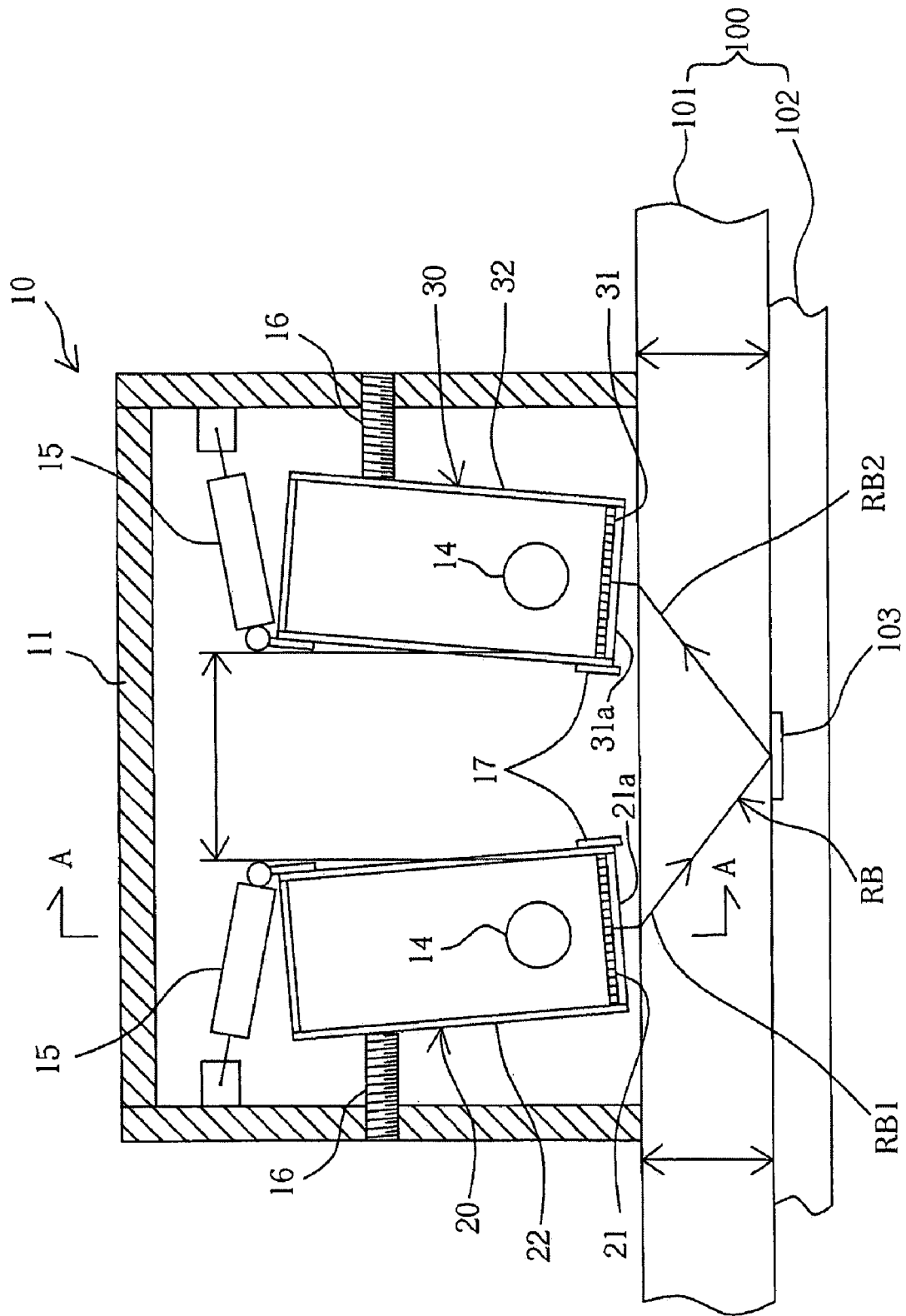
FIG. 1 is a longitudinally cross sectional view of a scanning head in an ultrasonic test apparatus according to the present invention.

1: Ultrasonic test apparatus, 2: PC, 3: A/D, 4: Filter, 5: Burst wave emitter/receiver, 6: Preamplifier, 7: Driver, 8: Scanner, 10: Scanning head, 11: Frame, 13: Support, 14: Shaft, 15: Spring, 16: Adjusting screw, 17. Shielding member, 18: Bearing, 19: Retaining screw, 20: Emitter, 21: Oscillator, 21a: Acoustic matching layer, 22: Casing, 30: Receiver, 31: Oscillator, 31a: Acoustic matching layer, 32: Casing, 100: Test piece, 101: CFRP material, 102: Insulating layer, 103: disbonding (defect).

BEST MODES FOR EMBODYING THE INVENTION

The present invention will be described in more detail referring to the accompanying drawings.

FIG. 3 illustrates an ultrasonic test apparatus 1 according to the present invention where an ultrasonic wave is emitted from an emitter 20 in a scanning head 10 connected with a burst generator 5 controlled by a personal computer (PC) 2 and its reflection is received by a receiver 30 before transferred via a preamplifier 6, a filter 4, and an A/D 3 to the PC 2 where it is processed. The PC 2 is also arranged to drive a scanner 8 via a driver 7 and two-dimensionally scan the surface of a test piece 100 with the scanning head 10.

Figure 2:
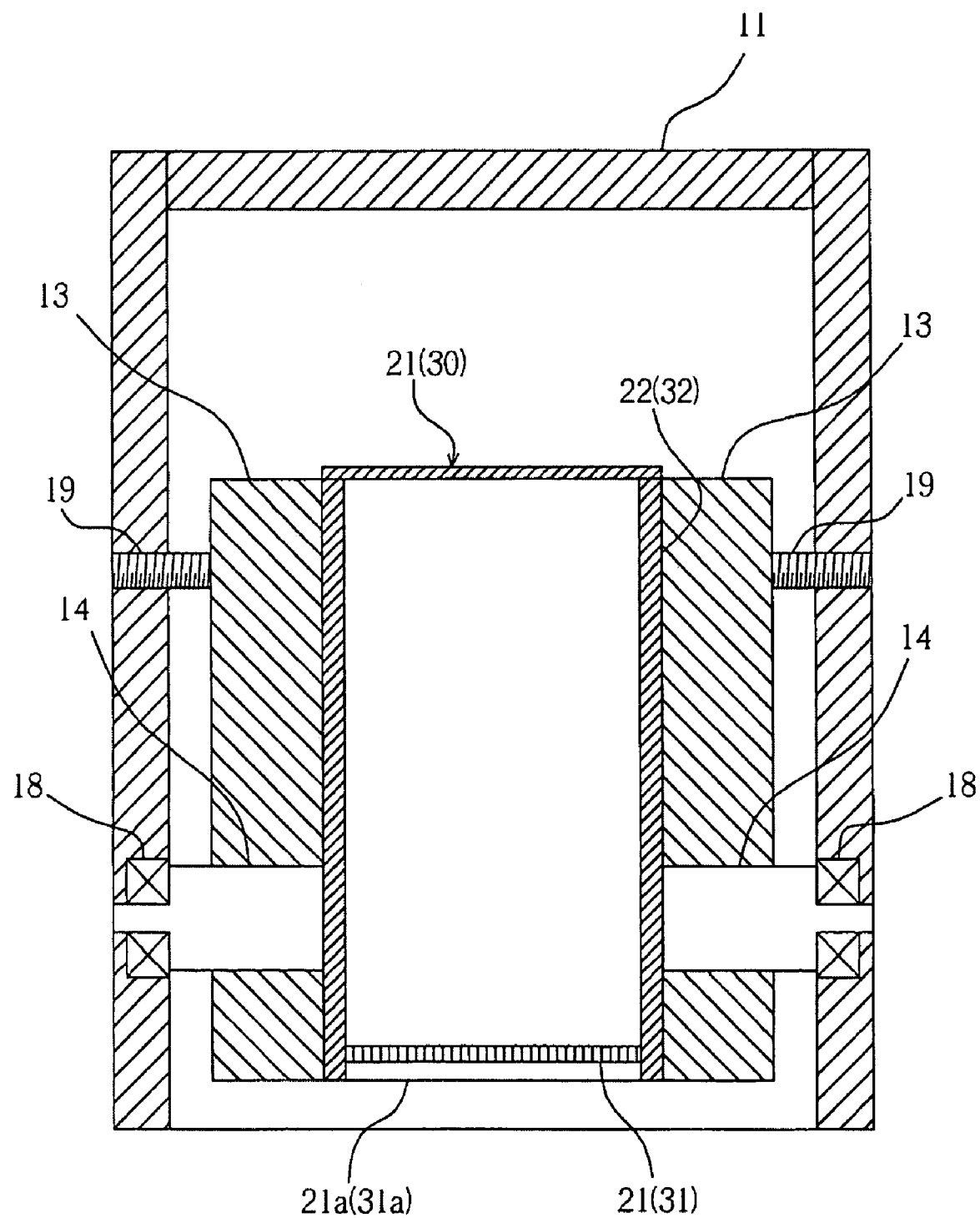
FIG. 2 is a cross sectional view taken along the line A-A of FIG. 1 where an emitter is located upright and the numerals in parenthesis represent identical components in a receiver.

The scanning head 10 includes the emitter 20 and the receiver 30 as shown in FIGS. 1 and 2. The emitter 20 and the receiver 30 have oscillators 21 and 31 provided respectively therein for emitting and receiving the ultrasonic wave and acoustic matching layers 21a and 31a thereof provided respectively for propagating the ultrasonic wave through the air. The oscillators 21 and 31 are accommodated in separate casings 22 and 32 respectively while each of them has a pair of shafts 14, 14 anchored by retaining members 13, 13 to both sides thereof and pivotably joined by bearings 18, 18 to a frame 11. The emitter 20 and the receiver 30 are supportingly joined at the top by springs 15 respectively to the frame 11 so that their upper sides remain urged and separated from each other. This allows the emitter 20 and the receiver 30 to be adjusted in the tilted state with adjusting screws 16, 16. The tilted state of the emitter 20 or the receiver 30 can be fixed by tightening a retaining screw 19. The emitter 20 and the receiver 30 are joined by the bearings 18 and the adjusting screws 16 or the retaining screws 19 to the frame 11. Since their casings 22 and 32 are separately provided, the emitter 20 and the receiver 30 are physically separated from each other thus to substantially inhibit the propagation of ultrasonic waves through a solid between the emitter 20 and the receiver 30.

The test piece 100 in this embodiment may, for example, be a composite material which comprises a CFRP material 101 and an insulating layer 102 of an elastic material, such as silicon rubber, bonded to each other for use in the space. More particularly, the interface between the CFRP material 101 and the insulating layer 102 is a target area to be inspected for any defect 103.

FIG. 4 illustrates a direct path RA through the air and a reflection path RB between the oscillator 21 in the emitter 20 and the oscillator 31 in the receiver 30. The direct path RA of the ultrasonic wave extends directly from the oscillator 21 through the air to the oscillator 31. The reflection path RB is a sum of two paths Rb1 and Rb4 through the air and two paths Rb2 and Rb3 of the ultrasonic wave incoming and reflecting in the interface between the CFRP material 101 and the insulating layer 102 of the test piece to be inspected.

It is now assumed that the CFRP material 101 has a thickness of T=15 mm, the horizontal distance between the two oscillators 21 and 31 is W=16 mm, and the distance between the CFRP material 101 and the two oscillators 21 and 31 is d=5 mm. While each of the paths Rb1 and Rb4 is substantially equal to d, each of the paths Rb2 and Rb3 is expressed by $T \times 2^{0.5}$. Also, the speed of propagation of ultrasonic wave through the air is v1=340 m/s and the speed of propagation of ultrasonic wave through the CFRP material 101 is v2=2780 m/s. Accordingly, the time ta for the propagation along the direct path RA through the air is expressed by:

$$ta = 16(\text{mm})/0.340(\text{mm}/\mu s) = 47.1\ \mu s$$

Also, the time tb for the propagation along the reflection path RB is expressed by:

$$tb = 5(\text{mm}) \times 2/0.340(\text{mm}/\mu s) + 15(\text{mm}) \times 2^{0.5} \times 2/2.78 (\text{mm}/\mu s) = 44.7\ \mu s$$

Each of the Rb2 and Rb3 is calculated to $15(\text{mm}) \times 2^{0.5}$, assuming that the ultrasonic wave is propagated at an angle of 45 degrees to the thickness throughout the CFRP material. As the result, tb<ta is established. In other words, the reflection of the ultrasonic wave is separated with time from the directly propagated component. According to the present invention, while the ultrasonic wave is propagated into a relatively greater depth, its reflected component can definitely be separated from the direct component through favorably controlling ta and tb along the paths RA and RB. Shields 17 are provided in the form of aluminum strip which are equal in the width to the emitter 20 and the receiver 30 for causing the ultrasonic wave to detour and substantially increasing the direct path RA through the air. In addition, another shielding 17' may be disposed to further increase the direct path RA through the air as shown in FIG. 4. The thickness of the CFRP material 101 is not limited to 15 mm in the embodiment described above. It is also noted that any defect in the CFRP material 101 as well as the interface can be detected through examining a difference in the time of the propagation between the two components of the ultrasonic wave.

Figure 5:
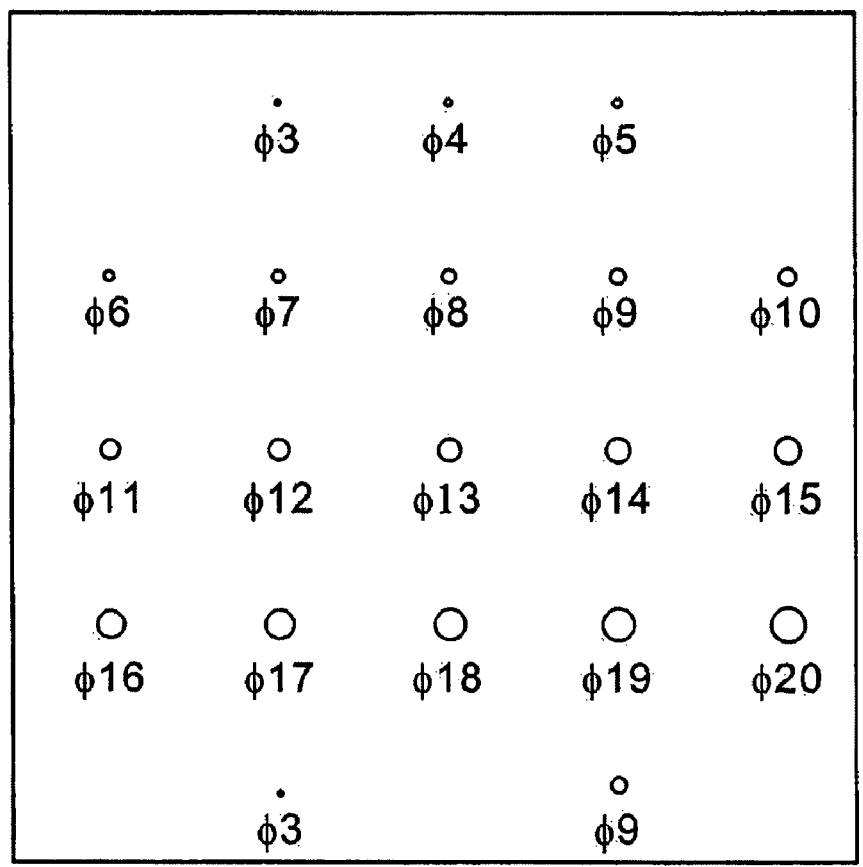
FIG. 5 is a plan view of a test piece which carries simulated disbanding defects at a diameter of 3-20 mm.
Figures 6A, 6B:
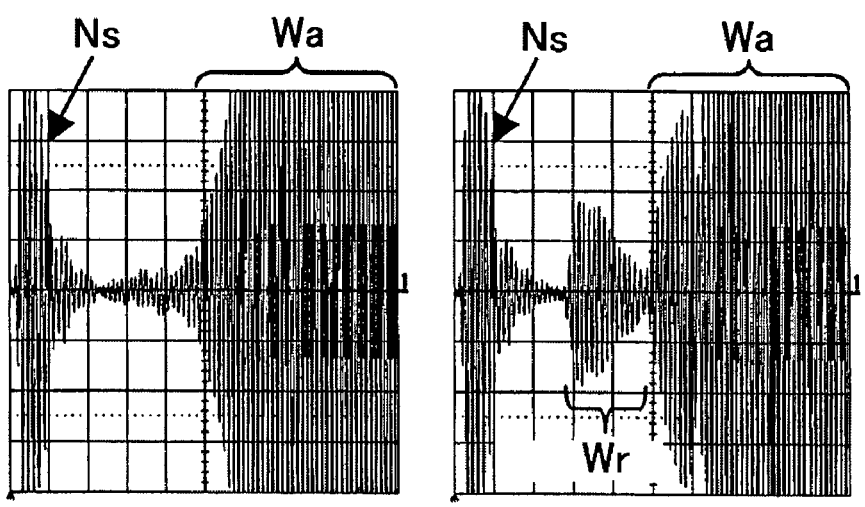
FIG. 6 is a graphic diagram showing the waveform of received waves in the test method, where FIG. 6a exhibits no defect while FIG. 6b indicates a disbanding defect with Ns representing an emitted noise, Wa representing a wave propagated through the air, and Wr representing a disbanding defect.
Figure 7:
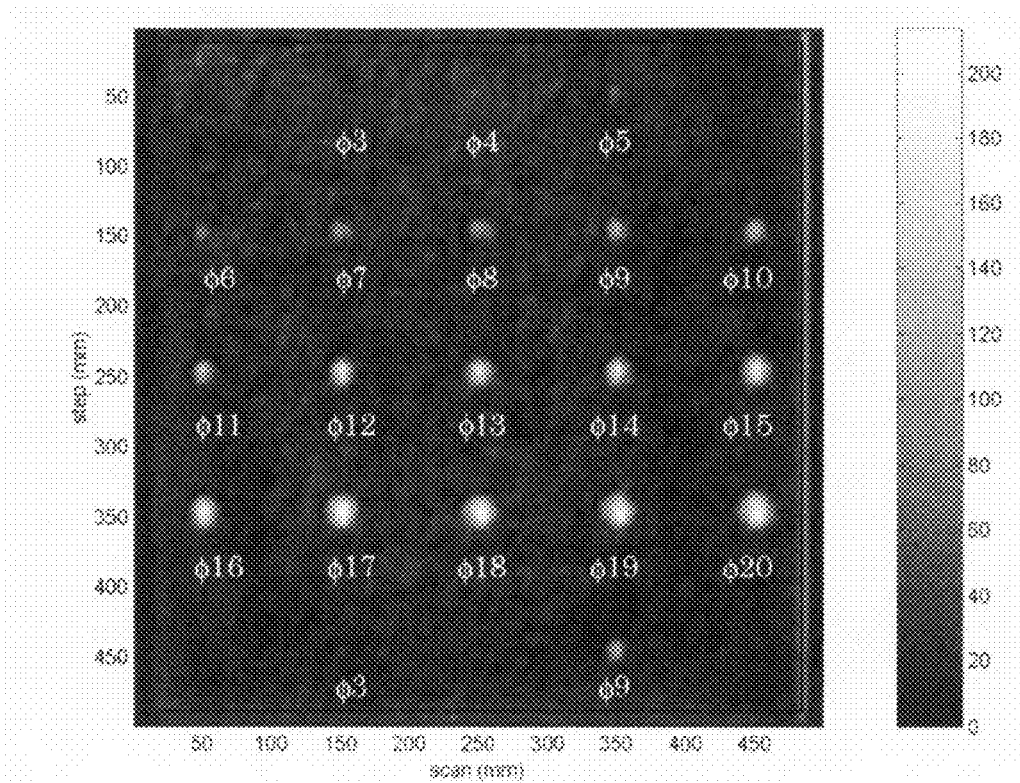
FIG. 7 illustrates a C scope image showing a result of inspection of a test piece made of a CFRP material at a thickness of 15 mm, using the test method according to the present invention.

Another example of the test will now be described using a test piece which contains a group of disbonding defects at a range of diameter, 3-20 mm, as shown in FIG. 5. The disbonding defects in the test piece 100 are developed in a fluorine resin sheet disposed between the CFRP layer 101 and the insulating layer 102. The oscillators 21 and 31 in the emitter 20 and the receiver 30 respectively are sized of 14×20 mm and has a nominal frequency of 400 kHz. FIG. 6 illustrates received waveforms of the ultrasonic wave, where the waveform in FIG. 6a exhibits no disbanding defect while the waveform in FIG. 6b indicates a disbanding defect. The waveform shown in FIG. 6b has a transmission noise followed by a disbonding defect reflected wave which is separated from the wave propagated through the air. FIG. 7 is a C scope image showing a result of defect inspection using the method of the present invention, where a test piece made of a CFRP material at a thickness of 15 mm is inspected and its simulated defects are clearly detected.

Figure 8:
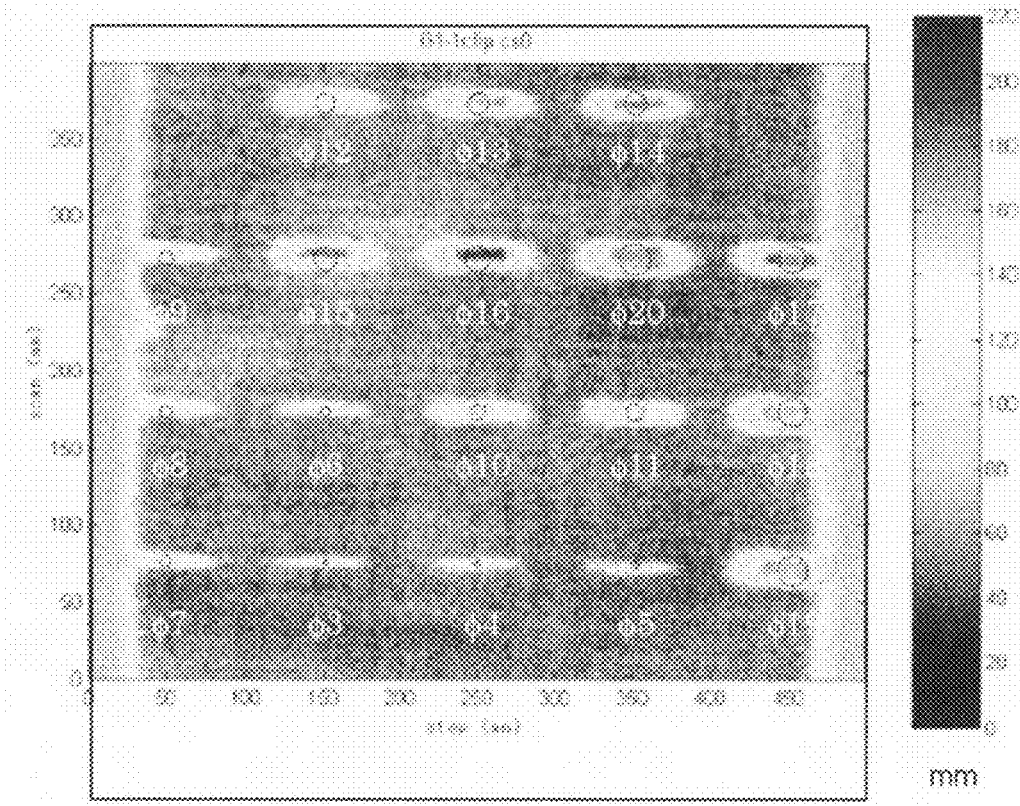
FIG. 8 illustrates a C scope image showing a result of inspection of a test piece made of a CFRP material at a thickness of 3 mm, using a plate wave transmission type non-contact test method, where denoted by the blank circle is an artificial defect in a poly fluorinated ethylene sheet.
Figure 9:
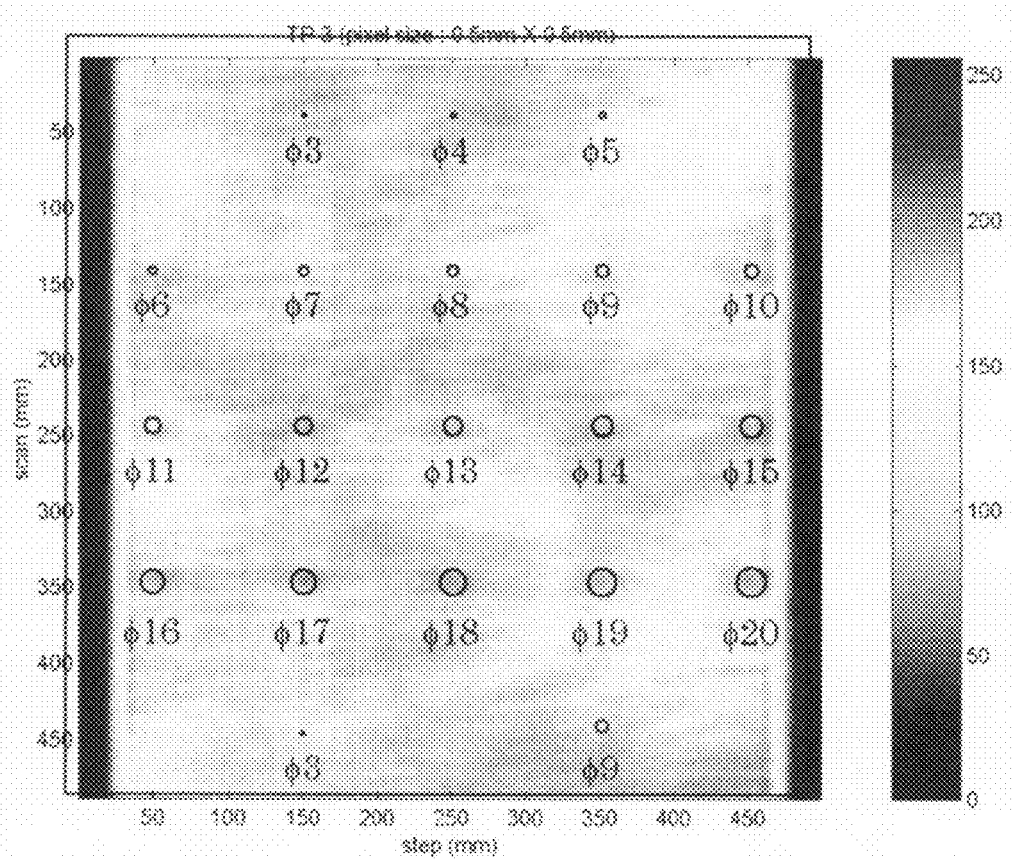
FIG. 9 illustrates a C scope image showing a result of inspection of a test piece made of a CFRP material at a thickness of 15 mm, using the plate wave transmission type non-contact test method.
Figure 10:
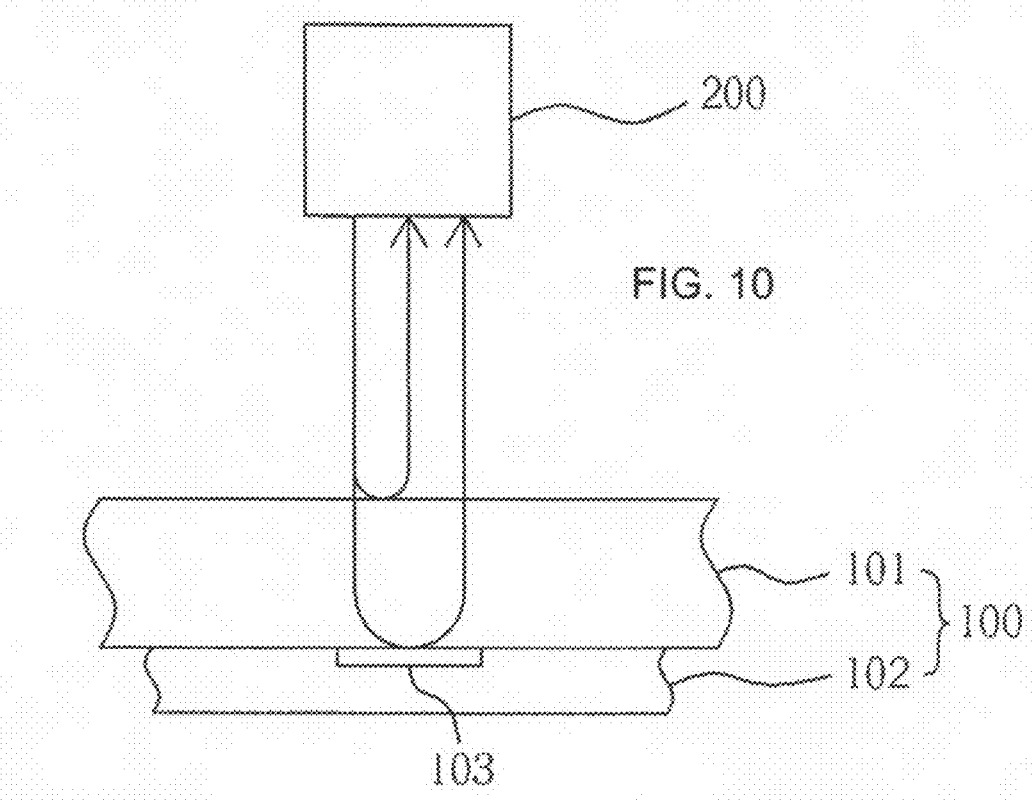
FIG. 10 is a view showing a probe and its periphery using a conventional reflection test method.
Figure 11A:
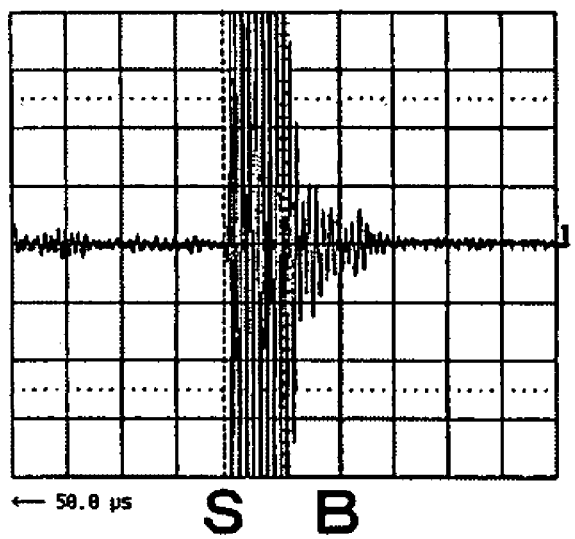
FIG. 11 is a graphic diagram showing the waveform of received waves in the conventional reflection test method, where FIG. 11a exhibits no defect while FIG. 11b indicates a disbonding defect, in which the primary components are.
Figure 11B:
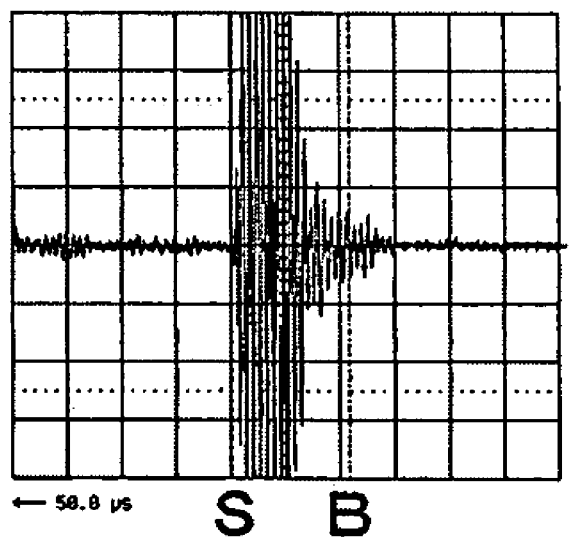

FIGS. 8 and 9 are C scope images showing results of defect inspection using a conventional plate wave transmission type non-contact inspection method. The results of defect inspection shown in FIGS. 8 and 9 are from test pieces made of a CFRP material at a thickness of 3 mm and a thickness of 15 mm respectively. While the conventional plate wave transmission type inspection method fails to satisfactorily detect the simulated defects on the thick test pieces, the method of the present invention is found higher in the performance of the inspection.

It would be understood that the ultrasonic test instrument, the structure and material of a test piece, and the resultant measurements according to the present invention are not limited to those described in the embodiment and various modifications may be made without departing from the scope of the present invention.

INDUSTRIAL APPLICABILITY

The present invention is applicable to a non-contact ultrasonic inspection method and a non-contact ultrasonic inspection apparatus for inspecting, for example, spacecraft materials and aircraft materials in layer forms. The method may be utilized for inspecting any defect in fiber reinforced plastics such as GFRP (grass fiber reinforced plastics), KFRP (Kepler (a tradename) fiber reinforced plastics), and CFRP (carbon fiber reinforced plastics) and in composite materials, at the interface between an FRP material and a rubber or honeycomb material.

What is claimed is:

1. An ultrasonic test method for emitting an ultrasonic wave from a probe provided at one side of a test piece and receiving the reflection of the ultrasonic wave, characterized in that the probe comprises an emitter and a receiver for emitting and receiving the ultrasonic wave through the gaps of air between the emitter and the test piece and between the test piece and the receiver, wherein the emitter, the receiver, and the test piece are relatively located in such a relationship that the duration of time for directly propagating the ultrasonic wave through the gap of air between the emitter and the receiver is longer than the duration of time for propagating the reflection of the ultrasonic wave.

2. An ultrasonic test method according to claim 1, wherein the propagation of the ultrasonic wave through a solid between the emitter and the receiver is interrupted.

3. An ultrasonic test method according to claim 1, wherein a casing for the emitter and a casing for the receiver are provided separately.

4. An ultrasonic test method according to claim 1, wherein a shielding member is provided at the interface between the emitter and the receiver.

5. An ultrasonic test method according to claim 1, wherein the emitter and the receiver are joined movably and separately to a frame.

6. An ultrasonic test method according to claim 1, wherein the test piece is a material in layers.

7. An ultrasonic test apparatus for use with the ultrasonic test method disclosed in any of claims 1 to 6, comprising an emitter and a receiver for emitting and receiving the ultrasonic wave through the gaps of air between the emitter and the test piece and between the test piece and the receiver, wherein the emitter, the receiver, and the test piece are relatively located in such a relationship that the duration of time for directly propagating the ultrasonic wave through the gap of air between the emitter and the receiver is longer than the duration of time for propagating the reflection of the ultrasonic wave.

* * * * *